United States Patent
Stankowiak

(10) Patent No.: US 9,539,521 B2
(45) Date of Patent: Jan. 10, 2017

(54) METHOD FOR REPROCESSING AIRCRAFT DE-ICING AGENTS COMPRISING GLYCOL

(71) Applicant: Clariant International Ltd., Muttenz (CH)

(72) Inventor: Achim Stankowiak, Altoetting (DE)

(73) Assignee: CLARIANT INTERNATIONAL LTD., Muttenz (CH)

( * ) Notice: Subject to any disclaimer, the term of this patent is extended or adjusted under 35 U.S.C. 154(b) by 0 days.

(21) Appl. No.: 14/896,603

(22) PCT Filed: May 23, 2014

(86) PCT No.: PCT/EP2014/001413
§ 371 (c)(1),
(2) Date: Dec. 7, 2015

(87) PCT Pub. No.: WO2014/198379
PCT Pub. Date: Dec. 18, 2014

(65) Prior Publication Data
US 2016/0129366 A1    May 12, 2016

(30) Foreign Application Priority Data

Jun. 13, 2013 (DE) .................. 10 2013 009 949

(51) Int. Cl.
*C09K 3/18* (2006.01)
*B01D 1/22* (2006.01)
*C07C 29/80* (2006.01)

(52) U.S. Cl.
CPC .................. *B01D 1/22* (2013.01); *C07C 29/80* (2013.01); *C09K 3/185* (2013.01)

(58) Field of Classification Search
CPC ........... C09K 3/18; C09K 3/185; C07C 29/76; C07C 31/202
See application file for complete search history.

(56) References Cited

U.S. PATENT DOCUMENTS

| | | | |
|---|---|---|---|
| 4,358,389 A | 11/1982 | Konig-Lumer et al. | |
| 4,744,913 A | 5/1988 | Salvador et al. | |
| 5,411,668 A | 5/1995 | Pollmann et al. | |
| 5,535,877 A * | 7/1996 | Eastcott | B01D 3/346 159/16.1 |
| 6,265,625 B1 * | 7/2001 | Vansant | B01D 1/223 159/11.2 |
| 8,262,927 B2 | 9/2012 | Kropac et al. | |
| 2011/0263909 A1 * | 10/2011 | Stankowiak | C09K 3/185 568/868 |

FOREIGN PATENT DOCUMENTS

| | | |
|---|---|---|
| EP | 0637620 A2 | 2/1995 |
| EP | 1889658 A2 | 2/2008 |
| WO | 92/04956 A1 | 4/1992 |

OTHER PUBLICATIONS

English Abstract for WO 92/04956, Apr. 2, 1992.
International Search Report for PCT/EP2014/001413, Sep. 2, 2014.
English Translation of International Preliminary Report on Patentability for PCT/EP2014/001413, Sep. 2, 2014.

* cited by examiner

*Primary Examiner* — Anthony J Green
(74) *Attorney, Agent, or Firm* — Tod A. Waldrop

(57) ABSTRACT

The present invention relates to a method for reprocessing aircraft de-icing agents comprising glycol, in which (1) the used aircraft de-icing agent, which is possibly contaminated with runway de-icing agents, is collected in a suitable device, (2) the used aircraft de-icing agent collected in this manner is subsequently brought to a glycol content of between 50 and 75% by weight without or after only course prior separation of solid or suspended impurities by expelling water (3) and the concentrate obtained in this manner is separated into a water/glycol mixture and residue by means of a thin-film evaporator, and (4) the water/glycol mixture is collected.

7 Claims, No Drawings

METHOD FOR REPROCESSING AIRCRAFT DE-ICING AGENTS COMPRISING GLYCOL

The invention relates to a method for reprocessing used aircraft de-icing agents based on glycols.

Aircraft de-icing agents based on glycols are described for example in U.S. Pat. No. 4,358,389 and U.S. Pat. No. 4,744,913. They generally comprise (a) about 40 to 80% by weight of at least one glycol having 2 or 3 carbon atoms or of a diglycol having 4 to 6 carbon atoms, for example ethylene glycol, diethylene glycol, propylene glycol and the like, (b) 0.05 to 1.5% by weight of at least one polymeric component as thickener, for example from the group of polyacrylates, polymethacrylates, xanthan gum and cellulose derivatives, (c) 0.05 to 1% by weight of at least one surfactant, for example olefinsulfonates, alkylarylsulfonates, polyoxalkylates and the like, (d) at least one corrosion inhibitor in an effective amount, for example from the group of triazoles, imidazoles and/or phosphoric acid esters, and (e) at least one basic compound for adjusting the pH to from about 7.5 to 11 and (f) water as remainder to 100% by weight.

These aircraft de-icing agents are applied to the parts of the aircraft to be treated as they are (i.e. as concentrate) or following dilution with water for their preservation and/or for the freeing of ice and/or snow. The de-icing agent, which is now more or less diluted with melt water and contaminated with sand, rubber dust, oil, combustion residues and the like, flows from the treated parts of the aircraft into a collecting vessel and is referred to as wastewater from the aircraft de-icing or as used aircraft de-icing agent.

The used aircraft de-icing agents are sometimes disposed of with the help of a biological wastewater treatment plant. However—despite the good biodegradability of glycols—this leads to an undesired burden on the wastewater treatment plant, especially at low outside temperatures and reduced bacteria activity associated therewith, which is generally the case when using de-icing agents. A further disadvantage of this type of disposal of aircraft de-icing agents is the loss of the large amount of valuable glycol.

EP-A-0 637 620 discloses a method for reprocessing used aircraft de-icing agents based on glycols, in which (1) the used aircraft de-icing agent is firstly filtered to separate off the suspended impurities, (2) the filtrate obtained in step (1) is subjected to an ultrafiltration to separate off the polymeric thickeners, (3) the permeate obtained in step (2) is subjected to ultrafiltration with an anion exchanger and a cation exchanger to separate off any salts and ionic compounds present, and (4) the solution obtained in step (3) is distilled to the desired value to remove excess water and thus adjust the glycol content, (5) the glycol/water mixture obtained is supplied with suitable additives for use as aircraft de-icing agent.

EP-A-1 889 658 discloses a method for reprocessing glycol-containing aircraft de-icing agents in which they are subjected directly to a separation by means of a membrane, thus excluding a distillation in a subsequent method step. This demanding and complex method in terms of plant technology for reusing used aircraft de-icing agents only makes sense at airports which have a large demand for aircraft de-icing agent.

EP 2 382 279 discloses a method for reprocessing aircraft de-icing agents comprising glycol, in which (1) the used aircraft de-icing agent, possibly contaminated with runway de-icing agent, is collected in a suitable device, (2) the used aircraft de-icing agent is subsequently brought to a glycol content between 55 and 75% by weight without, or after only coarse, prior separation off of solid or suspended impurities, by expelling water at elevated temperature, (3) the concentrated used aircraft de-icing agent obtained in this way is transported to a central reprocessing plant, where it is subjected to a fine distillation, and where (4) the glycol is produced as distillate of the fine distillation.

It has now been observed that the glycol recovered according to the prior art and incorporated into de-icing agents has an only inadequate pH stability. It comprises a fraction of glycol esters and other impurities, which rules out, considerably hinders, or permits only to a limited extent, further use as aircraft de-icing agents.

The object of the present invention is to propose a simple and cost-effective method which makes it possible to largely recover and reuse in particular the glycols from used aircraft de-icing agents, and where the reusability of the glycols is retained. The method should be able to be carried out with low plant complexity, meaning that operation of a corresponding plant in an airport is possible. The method should produce a reprocessed product with the fewest possible by-products, meaning that its further processing to a new aircraft de-icing agent does not adversely affect its service life. Furthermore, the input of energy should be as low as possible.

The present invention therefore provides a method for reprocessing aircraft de-icing agents comprising glycol, in which (1) the used aircraft de-icing agent, possibly contaminated with runway de-icing agent, is collected in a suitable device, (2) the thus collected used aircraft de-icing agent is subsequently brought to a glycol content between 50 and 75% by weight without, or after only coarse, prior separation off of solid or suspended impurities, by expelling water, (3) and the thus obtained concentrate is separated by means of a thin-film evaporator into a water/glycol mixture and a residue, and (4) the water/glycol mixture is collected.

In step 2, water is expelled to the extent that the concentrate obtained therefrom has a glycol content of preferably 55 to 70% by weight. The expulsion of the water preferably takes place at elevated temperature. However, water can also be drawn off by reducing the pressure, or by reduction in pressure and elevated temperature.

In step 3, the concentrate obtained from the used aircraft de-icing agent is fed to the thin-film evaporator to recover a purified water/glycol mixture. The water/glycol mixture is obtained as distillate of the thin-film evaporator. The residue which leaves the thin-film evaporator is discarded in one embodiment of the invention. In another embodiment, the residue is again fed to a thin-film evaporator, and the distillate thus obtained can be combined with the distillate obtained during the first pass.

The operating conditions of the thin-film evaporator are to be selected such that the water/glycol mixture that is formed has a glycol content of preferably 30 to 90% by weight, in particular 45 to 80% by weight, specifically 45-65% by weight, for example 45-60% by weight of glycol.

In a preferred embodiment, the glycols are glycols having 2 or 3 carbon atoms or diglycols having 4 to 6 carbon atoms, for example ethylene glycol, diethylene glycol or propylene glycol. Particular preference is given to propylene glycol and monoethylene glycol, in particular propylene glycol. Between steps 2 and 3, i.e. drawing off of the water and thin-film evaporation, the intermediate product obtained from step 2 can be adjusted to an alkaline pH using aqueous hydroxide solution, preferably using sodium hydroxide solution or potassium hydroxide solution.

The used aircraft de-icing agent is passed from the site where the aircrafts are de-iced in the airport grounds to a suitable container such as a storage tank or a collecting vessel. Prior to entering the storage tank or a collecting vessel, the used aircraft de-icing agent can be filtered in order to remove coarse impurities.

From there, the used aircraft de-icing agent is brought to a suitable device in which the water can be partially expelled, preferably by heating. Here, observing CSB limits in the condensate, depending on local regulations, has to be taken into consideration. The glycol content in the concentrate from the water expulsion is between 50 and 75% by weight of glycol. Then, the concentrate obtained in this way is passed to the thin-film evaporator. The operating conditions of the thin-film evaporator are for example:

Jacket temperature: 140-160° C.
Head temperature: 50-104° C.
Pressure: 80-120 mbar
Head bottoms ratio: approx. 1:1 to 2:1

The distillate obtained from the thin-film evaporator requires no further work-up. It can be further processed directly by adding suitable additives to give a new aircraft de-icing agent. It may be necessary to adjust the glycol content according to the specification by adding water or glycol.

The method according to the invention is particularly suitable for aircraft de-icing agents which the internationally valid standards and specifications, as stipulated in AMS 1424 and AMS 1428.

Such aircraft de-icing agents comprise, besides water, for example:

(a) 50 to 95% by weight of glycols having 2 or 3 carbon atoms or diglycols having 4 to 6 carbon atoms, (b) 0 up to 0.8% by weight, preferably 0 to 0.5% by weight, of water-soluble polymers from the group of polyacrylates and polymethacrylates as thickeners, (c) 0.01 to 1% by weight of surfactants, preferably from the group of anionic surfactants, for example sulfonates such as olefinsulfonates and alkylbenzenesulfonates, (d) 0.001 to 0.1% by weight of corrosion inhibitor, e.g. salts of phosphoric acid and succinic acid.

The stated composition refers to the aircraft de-icing agent prior to its use.

The desired grade of the glycols obtained by the method according to the invention is stipulated by the following criteria:

(a) a surfactant concentration of less than 100 ppm (b) a glycol content of 30-90% by weight, preferably 45-80% by weight, specifically 45-60% by weight (c) a glycolic acid content of less than 100 ppm, preferably less than 50 ppm (d) a formic acid content of less than 100 ppm, preferably less than 50 ppm (e) a lactic acid content of less than 100 ppm, preferably less than 50 ppm (f) an acetic acid content of less than 100 ppm, preferably less than 50 ppm (g) a propionic acid content of less than 100 ppm, preferably less than 50 ppm The desired content of glycol esters of the acids specified under (c) to (g) is at most as great as the content of the acids.

The method according to the invention offers considerable advantages compared to the prior art.

1. One distillation column less is required than for distillative reprocessing methods. This is an essential part of an investment into a recycling plant which is to be installed directly at the airport or in its vicinity.

2. The product obtained from the thin-film evaporator (with 30 to 90% by weight glycol content) was thermally treated significantly more gently than in distillative reprocessing methods; it was subjected to elevated temperatures only briefly in the thin-film evaporator. As a result of this, the content of by-products in the water/glycol mixture obtained in this way is very low.

3. In accordance with the method of the prior art, firstly all of the water is distilled off in order to then use it again in the production process after the fine distillation. The method according to the invention immediately leads to a usable water/glycol mixture, which saves energy to a considerable extent.

EXAMPLE 1

Concentrated, used aircraft de-icing agent based on propylene glycol with a water content of 43% (the content of propylene glycol was therefore between 56 and 57% by weight) was adjusted to an alkaline pH using 45% strength aqueous KOH and subjected to thin-film evaporation.

Operating conditions of the thin-film evaporator:
Jacket temperature: 150° C.
Head temperature: 55-76° C.
Pressure: 100 mbar
Head bottom ratio: approx. 1:1 to 2:1

The bottom was then subjected again to thin-film evaporation.

Operating conditions of the thin-film evaporator:
Jacket temperature: 150° C.
Head temperature: 90-104° C.
Pressure: 100 mbar
Head bottom ratio: approx. 2:1

The propylene glycol content of the combined distillates was approx. 47%.

EXAMPLE 2

Concentrated used aircraft de-icing agent based on propylene glycol with a water content of 43% (the content of propylene glycol was therefore between 56 and 57% by weight) was adjusted to an alkaline pH using 45% strength aqueous KOH and subjected to thin-film evaporation.

Operating conditions of the thin-film evaporator:
Jacket temperature: 150° C.
Head temperature: 80-90° C.
Pressure: 100 mbar
Head bottom ratio: approx. 2:1

The bottom was then subjected again to thin-film evaporation.

Operating conditions of the thin-film evaporator:
Jacket temperature: 150° C.
Head temperature: 80-98° C.
Pressure: 100 mbar
Head bottom ratio: approx. 2:1

The propylene glycol content of the combined distillates was approx. 49%. The table below shows the properties of the product obtained from the thin-film evaporation.

|  | Example | |
|---|---|---|
|  | 1 | 2 |
| Water content (DIN 51777) [%] | 53.6 | 51 |
| Surfactant content [ppm] | <50 | <50 |
| Glycolic acid [ppm] | <20 | <20 |
| Formic acid [ppm] | <20 | <40 |
| Lactic acid [ppm] | <40 | <20 |
| Acetic acid [ppm] | <20 | <20 |
| Propionic acid [ppm] | <20 | <20 |

The invention claimed is:

1. A method for reprocessing an aircraft de-icing agent comprising glycol, in which
   (1) a used aircraft de-icing agent, possibly contaminated with runway de-icing agent, is collected in a suitable device,
   (2) the collected used aircraft de-icing agent is subsequently brought to a glycol content between 50 and 75% by weight without, or after only coarse, prior separation off of solid or suspended impurities, by expelling water, to form a concentrate,
   (3) and the obtained concentrate is separated by means of a thin-film evaporator into a water/glycol mixture and a residue, and
   (4) the water/glycol mixture is collected.

2. The method as claimed in claim 1, in which the separation off of solid or suspended impurities in step (2) involves a coarse filtration.

3. The method as claimed in claim 1, in which the water/glycol mixture comprises, besides water,
   (a) 50 to 95% by weight of glycols having 2 or 3 carbon atoms or diglycols having 4 to 6 carbon atoms,
   (b) 0 up to 0.8% by weight of water-soluble polymers from the group of polyacrylates and polymethacrylates,
   (c) 0.01 to 1% by weight of surfactants, and
   (d) 0.001 to 1% by weight of corrosion inhibitor.

4. The method as claimed in claim 1, where the operating conditions of the thin-film evaporator are selected such that the water/glycol mixture has a glycol content of 30-90% by weight.

5. The method as claimed in claim 1, where the glycol is propylene glycol or monoethylene glycol.

6. The method as claimed in claim 1, where, between step 2 and step 3, the intermediate product obtained from step 2 is adjusted to an alkaline pH using an aqueous hydroxide solution.

7. The method as claimed in claim 1, where the operating conditions of the thin-film evaporator are selected such that the resulting water/glycol mixture has a glycol content of 45-65% by weight.

* * * * *